(12) United States Patent
Kuetting et al.

(10) Patent No.: US 10,888,424 B2
(45) Date of Patent: Jan. 12, 2021

(54) PROSTHETIC MITRAL VALVE COAPTATION ENHANCEMENT DEVICE

(71) Applicant: NVT AG, Muri (CH)

(72) Inventors: Maximilian Kuetting, Boeblingen (DE); Emilia Kawa, Hechingen (DE); Marcos Centola, Hechingen (DE)

(73) Assignee: MEDIRA AG, Muri (CH)

(*) Notice: Subject to any disclaimer, the term of this patent is extended or adjusted under 35 U.S.C. 154(b) by 36 days.

(21) Appl. No.: 15/387,336

(22) Filed: Dec. 21, 2016

(65) Prior Publication Data
US 2017/0172737 A1    Jun. 22, 2017

(30) Foreign Application Priority Data

Dec. 22, 2015 (EP) ..................... 15202121

(51) Int. Cl.
*A61F 2/24* (2006.01)

(52) U.S. Cl.
CPC ............ *A61F 2/246* (2013.01); *A61F 2/2418* (2013.01); *A61F 2/2448* (2013.01); *A61F 2/2457* (2013.01);
(Continued)

(58) Field of Classification Search
CPC ...... A61F 2220/0008; A61F 2230/0069; A61F 2/2448; A61F 2/246; A61F 2/2418; A61F 2/2457; A61F 2/2454; A61F 2/24
See application file for complete search history.

(56) References Cited

U.S. PATENT DOCUMENTS

| 8,968,395 B2 | 3/2015 | Hauser et al. |
| 9,579,199 B2 | 2/2017 | Hauser et al. |

(Continued)

FOREIGN PATENT DOCUMENTS

| EP | 3000437 A1 | 3/2016 |
| JP | 2007535342 A | 12/2007 |

(Continued)

OTHER PUBLICATIONS

European Search Report and Opinion in EP 15202121.8, dated Jun. 14, 2016, 8 pages.

(Continued)

*Primary Examiner* — Seema Mathew
(74) *Attorney, Agent, or Firm* — Rimon, P.C.

(57) ABSTRACT

The present invention relates to a prosthetic mitral valve device for implanting at the native mitral valve region of a heart. The prosthetic mitral valve coaptation enhancement device comprises a main body consisting of a stentframe and a valve element attached thereto, wherein the main body has a sealing section and a valve-bearing section, the valve-bearing section; the shape of the sealing section of the main body, in the compressed state, has a form that is adapted to the coaptation zone of the native mitral valve during systole, and the sealing section of the main body, the radial rigidity of the stentframe is lower than the radial rigidity of the valve-bearing section; the prosthetic mitral valve coaptation enhancement device further comprises at least one anchoring element, which anchoring element is coupled to the main body and is capable to anchor the main body within the native mitral valve region of a heart.

9 Claims, 6 Drawing Sheets

(52) U.S. Cl.
CPC ............. *A61F 2220/0008* (2013.01); *A61F 2220/0016* (2013.01); *A61F 2230/0069* (2013.01); *A61F 2250/006* (2013.01); *A61F 2250/0018* (2013.01)

(56) References Cited

U.S. PATENT DOCUMENTS

| | | | |
|---|---|---|---|
| 9,636,223 B2 | 5/2017 | Khalil et al. | |
| 9,839,517 B2* | 12/2017 | Centola | A61F 2/2418 |
| 9,931,206 B2* | 4/2018 | Weber | A61F 2/2418 |
| 10,052,204 B2* | 8/2018 | McLean | A61F 2/2436 |
| 10,285,810 B2* | 5/2019 | Schweich, Jr. | A61F 2/24 |
| 10,299,927 B2* | 5/2019 | McLean | A61F 2/2409 |
| 10,433,961 B2* | 10/2019 | McLean | A61F 2/2436 |
| 10,492,908 B2* | 12/2019 | Hammer | A61F 2/2418 |
| 10,646,360 B2* | 5/2020 | Stengel | A61F 2/82 |
| 2007/0185571 A1* | 8/2007 | Kapadia | A61F 2/2466 623/2.11 |
| 2009/0276040 A1* | 11/2009 | Rowe | A61B 17/0401 623/2.18 |
| 2010/0217382 A1* | 8/2010 | Chau | A61F 2/2457 623/1.26 |
| 2012/0116498 A1* | 5/2012 | Chuter | A61F 2/2412 623/1.26 |
| 2013/0325110 A1 | 12/2013 | Khalil et al. | |
| 2014/0012763 A1 | 1/2014 | Madden et al. | |
| 2014/0031928 A1 | 1/2014 | Murphy et al. | |
| 2014/0214159 A1* | 7/2014 | Vidlund | A61F 2/2409 623/2.14 |
| 2015/0127097 A1 | 5/2015 | Neumann et al. | |
| 2015/0142103 A1* | 5/2015 | Vidlund | A61F 2/2418 623/2.17 |
| 2015/0173900 A1 | 6/2015 | Hauser et al. | |
| 2016/0089238 A1 | 3/2016 | Centola et al. | |
| 2017/0079780 A1* | 3/2017 | Schweich, Jr. | A61F 2/2412 |

FOREIGN PATENT DOCUMENTS

| | | |
|---|---|---|
| JP | 2008536592 A | 9/2008 |
| JP | 2008536592 A5 | 6/2009 |
| WO | 2005087140 A1 | 9/2005 |
| WO | 2006111391 A1 | 10/2006 |
| WO | WO 2013/178335 A1 | 12/2013 |

OTHER PUBLICATIONS

JP, Notice of Reason for Refusal for JP patent application 2016-244083, dated Feb. 19, 2019, 5 pages with additional 4 pages of English translation.

Fourth Office Action for Chinese Patent Application CN201611202471.6, dated May 25, 2020, 22 pages with extra 17 pages of English language equivalent or summary.

* cited by examiner

PROSTHETIC MITRAL VALVE COAPTATION ENHANCEMENT DEVICE

CROSS REFERENCES TO RELATED APPLICATIONS

This application is claiming priority from European patent application EP 15202121.8, filed on Dec. 22, 2015. The entire content of this priority application is incorporated herein by reference.

BACKGROUND OF THE INVENTION

The present invention concerns an implantable prosthetic mitral valve coaptation enhancement device, in particular for treating mitral valve regurgitation and the use of such a device for treating diseased or otherwise dysfunctional mitral valves.

Nowadays, prosthetic mitral valve devices are used as a possible treatment of mitral valve insufficiency, also referred to as mitral regurgitation. Such prosthetic valves are delivered by traditional surgical implantation methods, or by less invasive percutaneous catheter or minimally invasive transapical methods.

The mammalian heart comprises four chambers, i.e. two atria, which are the filling chambers, and two ventricles, which are the pumping chambers. In a mammalian heart, there are four heart valves present which normally allow blood to flow in only one direction through the heart, whereby a heart valve opens or closes depending on the differential blood pressure on each side.

The four main valves in the heart are the mitral valve, representing a bicuspid valve, and the tricuspid valve, which are between the upper atria and the lower ventricles, respectively, and thus are called atrioventricular (AV) valves. Further, there are the aortic valve and the pulmonary valve which are in the arteries leaving the heart. The mitral valve and the aortic valve are in the left heart and the tricuspid valve and the pulmonary valve are in the right heart.

The valves incorporate leaflets or cusps, wherein each valve has three cusps, except for the mitral valve, which only has two.

The mitral and the tricuspid valve are situated, respectively, between the atria and the ventricles and prevent backflow from the ventricles into the atria during systole. They are anchored to the walls of the ventricles by chordae tendineae which prevent the valves from inverting. The chordae tendineae are attached to papillary muscles that cause tension to better hold the valve. Together, the papillary muscles and the chordae tendineae are known as the subvalvular apparatus. While the function of the subvalvular apparatus is to keep the valves from prolapsing into the atria when they close, the subvalvular apparatus, however, has no effect on the opening and closure of the valves, which is caused entirety by the pressure gradient across the valve.

During diastole, a normally-functioning mitral valve opens as a result of increased pressure from the left atrium as it fills with blood (preloading). As atrial pressure increases above that of the left ventricle, the mitral valve opens. Opening facilitates the passive flow of blood into the left ventricle. Diastole ends with atrial contraction, which ejects the final 20% of blood that is transferred from the left atrium to the left ventricle, and the mitral valve closes at the end of atrial contraction to prevent a reversal of blood flow.

Several different kinds of valve disorders are known, such as stenosis, which occurs when a heart valve doesn't fully open due to stiff or fused leaflets preventing them from opening properly, or prolapse, where the valve flaps do not close smoothly or evenly but collapse backwards into the heart chamber they are supposed to be sealing off.

Valve regurgitation (backward flow) is also a common problem, and occurs when a heart valve doesn't close tightly, as a consequence of which the valve does not seal and blood leaks backwards across the valve. This condition—also called valvular insufficiency—reduces the heart's pumping efficiency: When the heart contracts blood is pumped forward in the proper direction but is also forced backwards through the damaged valve. As the leak worsens, the heart has to work harder to make up for the leaky valve and less blood may flow to the rest of the body. Depending on which valve is affected, the condition is called tricuspid regurgitation, pulmonary regurgitation, mitral regurgitation, or aortic regurgitation.

Mitral regurgitation, i.e. the abnormal leaking of blood from the left ventricle through the mitral valve and into the left atrium when the left ventricle contracts, is a common valvular abnormality, being present in 24% of adults with valvular heart disease and in 7% of the population 75 years of age. Surgical intervention is recommended for symptomatic severe mitral regurgitation or asymptomatic severe mitral regurgitation with left ventricular dysfunction or enlargement. Surgical treatment of severe degenerative mitral regurgitation has evolved from mitral valve replacement to mitral valve repair, since a mitral valve repair has proven to produce superior outcomes.

Meanwhile, as already mentioned at the outset, mitral valve repair and replacement has also been achieved using minimally invasive procedures. The desire for less invasive approaches is linked with the fact that a significant proportion of patients, especially elderly persons or those with significant comorbidities or severe left ventricular dysfunction, are not referred for (open heart) surgery.

Various percutaneous technologies have emerged and are at different stages of development. Current percutaneous technologies for mitral valve repair or replacement are, e.g., percutaneous mitral valve replacement, enhanced mitral coaptation, edge-to-edge-percutaneous mitral valve repair (plication), percutaneous chordal repair, percutaneous mitral annuloplasty, and left ventricle remolding.

However, the different percutaneous repair approaches do still not offer the same degree of efficacy as a surgical repair of the mitral valve.

While the technology of percutaneous mitral valve replacement is a possible alternative in a selected group of patients with a low probability of successful repair, the challenges of this technique are very high: the mitral annulus has an asymmetrical saddle shape, and different anchoring designs might be required for different mitral regurgitation etiologies. Further, left ventricular outflow obstruction might occur due to retained native valve tissue and paravalvular leaks might also pose problems.

E.g., WO 2013/178335 A1 discloses an implantable device for improving or rectifying a heart valve insufficiency, such as mitral valve regurgitation, and comprises a contact strip attached to a closure element, which contact strip forms a loop in the atrium thus contacting the inner wall of the heart and attaching the device therein.

Further, US 2014/012763 A1 discloses a mitral valve prosthesis including a self-expandable frame and two or more engagement arms. The self-expandable frame carries a valve. Each of the engagement arms corresponds to a native mitral valve leaflet. The prosthesis also comprises anchor attachment points, by means of which anchors are attached for anchoring the prostheses in the heart.

In view of the above, there still is the need for a heart valve prosthesis by means of which heart valve regurgitation can be efficiently treated, while at the same time traumatic impact on the heart is minimized.

SUMMARY OF THE INVENTION

According to the invention, this and other objects is solved by a prosthetic mitral valve device for implanting at the native mitral valve region of a heart, the native mitral valve having a native annulus and native valve leaflets, the prosthetic mitral valve coaptation enhancement device comprising a main body consisting of a stentframe and a valve element attached thereto, the main body comprising a length and a lumen being defined by a proximal end and a distal end, and configured for placement within the native valve region of the heart, the stentframe being radially compressible to a radially compressed state for delivery into the heart and self-expandable from the compressed state to a radially expanded state, wherein the main body has a sealing section and a valve-bearing section, the valve-bearing section carrying a valve element; further, in the prosthetic device according to the invention, the shape of the sealing section of the main body, in the compressed state, has a form that is adapted to the coaptation zone of the native mitral valve during systole, and in the sealing section of the main body, the radial rigidity of the stentframe is lower than the radial rigidity of the valve-bearing section; in addition, the prosthetic mitral valve coaptation enhancement device further comprises at least one anchoring element, which anchoring element is coupled to the main body and is capable to anchor the main body within the native mitral valve region of a heart.

The present invention also concerns the use of the prosthetic mitral valve coaptation enhancement device in the treatment of mitral valve regurgitation of a patient in need thereof, preferably a human.

With the prosthetic mitral valve coaptation enhancement device according to the invention, the space left by malcoaptation of the native mitral leaflets can filled out, and, thus, mitral regurgitation can be reduced or even eliminated when placing the device according to the invention inside the annulus of a native mitral valve at the respective coaptation line.

With the dimensions of the presently described device being smaller than a native mitral annulus, the disclosed prosthetic mitral valve coaptation enhancement device allows filling of the ventricle through the device and alongside the device during diastole, and thus minimizes the gradient between the left atrium and ventricle.

According to the invention, the prosthetic mitral valve coaptation enhancement device, in the sealing section, in the compressed state, adapts to the coaptation line of the native mitral valve.

In a healthy heart, when the left atrium chamber contracts in late diastole. It sends blood to the larger, lower left ventricle chamber. When the lower ventricle chamber is filed and the mitral valve to the left atrium is closed, the ventricle undergoes isovolumetric contraction (contraction of the ventricle while the mitral valve is closed), marking the first stage of systole. The second phase of systole sends blood from the left ventricle to the aorta and body extremities.

The human mitral valve consists of two valve leaflets, namely the anterior leaflet (AMVL) and the posterior leaflet (PMVL), which are attached to two major papillary muscles in the left ventricle via small tendons (chordae tendineae) which ensure that the leaflets do not prolapse. In a healthy mitral valve, the leaflet edges meet and form a tight seal, a process called leaflet coaptation; as a consequence, healthy, normal heart valves allow blood to flow only in one direction.

As described in the introducing section above, when mitral valve closure is impaired and the leaflets do not seal properly, blood leaks and flows backwards from the left ventricle into the atrium, which may eventually result in pulmonary hypertension and pulmonary edema.

With the device according to the invention, a unidirectional flow is created, preventing flow from the ventricle to the atrium in systole and permitting flow from the atrium to the ventricle in diastole: The leaflets of the native mitral valve coapt against the implanted device according to the invention, thus sealing the mitral annulus during systole and recreating the valvular function of the structure. With the lower radial rigidity in the sealing section compared to the valve-bearing section, in connection with a circular. D- or crescent shape of the proximal end, it is guaranteed that the space left between the two malcoapting mitral leaflets is filled out without expanding the space and without forcing the not properly closed valve even further open.

Presently, the expression "adapts to the coaptation zone of the native mitral valve" in view of the sealing section means, that the sealing section has a shape and design such that it fits into and fills out the space left by the not property closing leaflets of the native, malfunctioning mitral valve. Preferably, the sealing section has a circular, D- or crescent shape, which transitions into a cylindrical shape along the length of the device, so that the valve-bearing section has a cylindrical shape.

Further, the expression "proximal end" of the main body is used to designate the inflow section of the lumen of the device's main body, i.e. the end of its lumen where blood enters to flow into the ventricle. Accordingly, the expression "distal end" of the lumen designates the outflow lumen end. i.e. the end where the blood exits the lumen.

Presently, and as generally understood, "D"- or "crescent-shape" as used herein means a shape that substantially resembles the letter "D", and/or is generally a shape produced when a substantially circular disk has a segment of another circle removed from its edge, so that what remains is a shape enclosed by two substantially circular arcs of different diameters which intersect at two points. In this connection, the expression "substantially" is meant to designate a form that has the described form/shape to a large, great or significant extend.

The overall shape of the main body according to the invention is tubular, with a diameter of the cross section at the proximal end being larger than the diameter of the cross-section of the distal end, thus conferring the main body a substantially cone-shaped or convex form.

Presently, and as generally understood, the term "stentframe" is meant to comprise a cylindrical, tubular, or otherwise shaped radially-expandable metal frame or body, and, thus, comprises any device or structure that adds rigidity, expansion force, or support to a prosthesis. A stentframe may also consist of substantially hollow expandable structures, which can be filled or inflated to reach their functional shape.

The metal frame of the stent members and elements of the device according to the invention can be laser cut or woven or braided or knitted or comprise an otherwise interconnected metal mesh.

According to an embodiment, in the device according to the invention the stentframe is preferably made of a shape-memory material, preferably Ninitol. Nitinol has been proven as suitable for implantable medical devices and used in different medical appliances.

The valve carried in the valve-bearing section of the prosthetic mitral valve coaptation enhancement device, can be created from human or animal donors. They can be created, e.g., from pericardium of human or any mammal, or from native leaflets from the heart or veins, or from any other biological material suitable for the intended purpose. Generally speaking, such valves are also called biological or tissue valves—as contrary to mechanical valves.

In the device according to the invention, the valve may comprise flexible materials, or a rigid mechanical valve mechanism is used, e.g. monoleaflet, bileaflet, ballcage, caged disc. Flexible materials include aortic valve leaflets harvested from animals, animal pericardial tissue, tissue engineered material, harvested human pericardial tissue or synthetic materials. The design may use one, two, three, or more individual leaflets of equal or different sizes.

Stent and/or stent grafts generally comprise, for example, a series of stent elements or, respectively, a wire framework made of a self-expanding material.

In an embodiment of the device according to the invention, the outer wall of the stentframe may or may not be entirely covered. A soft material may be used to cover the stentframe in order to reduce or minimize friction and in order not to promote adhesion of the mitral leaflets to the device. Examples for such soft materials are, e.g., pericardium, PTFE (potytetrafluoroethylene), etc.

The valve-bearing section may also represent single metal rings forming a metal mesh, the rings meandering circumferentially and being disposed successively in the valve-carrying stent-portion's longitudinal axis/direction, wherein the metal rings have a Z-shaped profile with pointed arches pointing alternately toward the proximal end and distal end of the device. The metal rings are, thus, indirectly connected via the skirt-portion of the valve.

Presently, the expressions "substantially cylindrical" or "a substantially cylindrical shape" or a "substantially cylindrical form" presently mean any three-dimensional form that has a certain length, and that has a substantially round cross section, wherein also forms are comprised the cross sections of which are, e.g., an ellipse, parabola, or hyperbola, and wherein the cross-section does not necessarily need to have a regular circumference, but also includes irregular circumferences, as long as the substantially cylindrical form of the valve carrying stent-portion is retained. Also, with the expression "substantially cylindrical" forms are comprised which conform or substantially conform to the treated valve anatomic annulus shape.

Similar, the expression "substantially continuous" in connection with the diameter of the substantially cylindrical shape of the valve-carrying stent-portion means that, generally, the diameter of the cylindrical form is about the same over its length, wherein it will be clear to one skilled in the art that there can be minor or slight variations in diameter due to manufacturing issues.

The components of the device, i.e. the sealing section and the valve-bearing section, can be variously sized (i.e.: length, diameter, etc.) as suitable for an intended use and as depending on the respective condition and shape and dimension of the patient's heart, while at the same time comprising the features of the device as claimed.

According to a preferred embodiment of the invention, the stentframe of the prosthetic device is self-expanding, wherein the device is configured, such, that it is convertible from a compressed state for introducing the device into a heart of a mammal to an expanded state within the heart.

According to a preferred embodiment, the valve-element, upon implantation of the device, is sized and configured such, that the native mitral valve's function is supported without replacing or impairing the native mitral valve's function.

With the "native mitral valve's function", presently, the opening and closing of the mitral valve, is meant, as far as the mitral valve is closing. The latter means that if the native mitral valve's function is impaired as such, i.e. prior to the implantation of the prosthetic device according to the invention, it does not property close leading to a leaking a mitral valve regurgitation. However, upon implantation of the device according to the invention, the leaflets of the diseased mitral valve can still perform a closing movement, while it is obvious that they will abut/coapt against the valve-bearing section of the prosthetic device.

When delivered by catheter, the method according to the invention can also include the step of inserting a delivery catheter including the prosthetic device, the implantable device being in a compressed state when loaded on the delivery catheter loading and upon inserting the device into the heart of a subject that requires the treatment, i.e. is suffering from mitral valve regurgitation.

The patient or subject in need of treating, i.e. the patient or subject suffering from mitral valve regurgitation, is a mammal, preferably a human.

As mentioned above, the invention also refers to an embodiment of the prosthetic mitral valve coaptation enhancement device, wherein the stentframe in the sealing section, in its expanded state, is substantially circular, D- or crescent-shaped and is adapted to the shape of and designed to be placed at the coaptation line of the native valve, wherein the crescent-shape transitions along the length of the main body towards the ventricular section into a substantially round shape.

According to a preferred embodiment of the prosthetic mitral valve coaptation enhancement device, the stentframe in the sealing section consists of a flexible structure such, that, in the compressed state, it conforms to the coaptation zone of the native mitral valve during systole, wherein the stentframe, in the sealing section, has a flexibility and rigidity that is lower than the flexibility and rigidity of the valve-bearing section.

In this connection, the expression "rigidity" as presently used, is meant to designate the mechanical property of the stentframe referring to the stiffness of the stentframe, which can be influenced not only by the material used for the stentframe but also by the overall design of the stentframe. Suitable techniques are known to one skilled in the art to compare the flexibility and rigidity of a stentframe (section) with the flexibility and rigidity of another stentframe (section), and include, e.g., bending tests, compression tests, etc., and the chosen rigidity/flexibility will depend on the information of the patient's condition.

According to a preferred embodiment, the prosthetic mitral valve coaptation enhancement device has a size enabling the sealing section being positionable at the level of the native mitral valve leaflets and the valve-bearing section being positionable distally in the left ventricle.

With this embodiment, the sealing section is designed to be close to the proximal (inflow) end of the lumen of the device's main body, and the valve-bearing section is designed to be close to the distal (outflow) end of the lumen.

According to another embodiment, the prosthetic mitral valve coaptation enhancement device has a configuration enabling the sealing section being positionable at the level of the native mitral valve leaflets and the valve-bearing section being positionable proximally in the right atrium.

This embodiment has the advantage that interference or contact with the subvalvular mitral apparatus (chordae tendinae, papillary muscles) and the left ventricle can be avoided in difficult anatomies.

The following embodiments describe alternatives of the anchoring element of the prosthetic mitral valve coaptation enhancement device of the invention:

In a preferred embodiment of the prosthetic mitral valve coaptation enhancement device of the invention, the anchoring element comprises one or more lengthy connecting elements, the connecting elements comprising a first end, a second end and a length extending there between, wherein the connecting element/s via its/their respective first end/s is/are coupled to the valve-bearing section, preferably to the distal (outflow) end, of the main body, and, via its/their respective second end/s, is/are coupleable to the ventricular apex.

In a refinement of this embodiment, the second end of the anchoring element is coupled to a plug element, which is sized and configured to be positionable in the ventricular apex of the heart, thereby piercing the apex.

According to another embodiment if the prosthetic mitral valve device of the invention, the anchoring element is a stent-based aortic valve prosthesis, coupled to the prosthetic mitral valve coaptation enhancement device via connecting elements to the distal outflow end.

In yet another embodiment of the prosthetic mitral valve coaptation enhancement device, the anchoring element comprises one or more generally U-shaped attachment arms, the attachment arm/s comprising a first end and a second end, respectively, wherein the second end comprises attachment means, preferably selected from a hook, a spike or an arrow, and wherein the attachment arms, via its/their respective first end is/are fixed to the stentframe at proximal inflow section, and via its/their respective second end are capable to anchor the main body in the tissue surrounding the mitral annulus.

According to another embodiment of the prosthetic mitral valve coaptation enhancement device of the invention, the anchoring element comprises one or more atrial substantially rigid lengthy connecting elements, the atrial lengthy connecting elements comprising a first end, a second end and a length extending there between, wherein the atrial lengthy connecting elements, via its/their respective first end/s is/are coupled to the sealing section, preferably to the proximal inflow end, of the main body, and, via its/their respective second end, is/are coupleable to the atrial wall, preferably via a atrial wall plug element, thereby piercing the wall.

In yet another embodiment of the prosthetic mitral valve coaptation enhancement device of the invention, the anchoring element comprises one or more septal lengthy connecting elements, the septal lengthy connecting elements comprising a first end, a second end and a length extending there between, wherein the septal lengthy connecting elements, via its/their respective first end/s is/are coupled to the valve-bearing section, preferably to the distal outflow end, of the main body, and, via its/their respective second end, is/are coupleable to a septal wall of the heart, preferably via a plug element, thereby piercing the septal wall.

According to a refinement of the latter embodiment, the septal wall is the septal wall of ventricle or of the atrium.

According to yet another embodiment of the prosthetic mitral valve coaptation enhancement device of the invention, the anchoring element is an expandable structure that is shaped and designed such, that it is positionable within the left atrial appendage, wherein the expandable structure, via lengthy flexible connecting means, is coupled to the proximal end of the main body.

In yet another embodiment of the prosthetic mitral valve coaptation enhancement device according to the invention, the anchoring element comprises one or more connecting element/s, the connecting element/s comprising a first end, a second end and a length extending there between, wherein the connecting element/s, via its/their respective first end/s is/are coupled to the valve-bearing section, preferably to the distal outflow end, of the main body, and, via its/their respective second end, is/are coupled to a clamping element fixable intraventricularly without piercing the apex.

According to another embodiment of the prosthetic mitral valve coaptation enhancement device of the invention, the anchoring element comprises one or more expandable structures that is/are designed such that the expandable structures are expandable and positionable within the pulmonary veins, thus anchoring the main body.

Presently, and as generally understood, a "plug element" is meant to comprise any suitable fastener enabling the fixation of the anchoring element in the ventricular apex, in the atrial wall and/or septal wall.

Further, as presently used herein and as generally understood, "lengthy connecting element" means any bar- or ligament-like structure the length of which is longer than its width. In some embodiments, the connecting means can be a wire, a bar, a ligament, a thread, or other, and by made from any inert material of sufficient strength generally used in the medical field.

In this connection, a "bar" element or "ligament" element or means is any lengthy structure of sufficient rigidity and flexibility for being coupled, via its one end, to the device according to the invention, and, via its second end, to a structure of the heart and/or to another anchoring element, e.g. a plug. The lengthy structure/bar/ligament element can be of any material suitable for these purposes, and is preferably of an inert, substantially rigid material, such as, metals, e.g. Nitinol, stainless steel. Titanium, polymers, e.g. polyether ether ketone (PEEK), polyoxymethylene (POM), polyether (PE), polyamide (PA), polytetrafluoroethylene (PTFE), which materials may also be reinforced by fibres to improve stability), ceramics, materials of animal or human origin or generally synthetic materials. The structures may also be substantially hollow structures, which are inflatable or fillable to attain their stability. They may also be combinations of the aforementioned. To promote the biocompatibility, the surface of the structures may be coated or otherwise treated.

Generally, and according to an embodiment of the invention, the prosthetic mitral valve coaptation enhancement device comprises a combination of one or more of the above discussed anchoring elements.

The invention also relates to the use of the device according to the invention for treating mitral valve regurgitation in a mammal, as well as to a method for treating mitral valve regurgitation in a mammal, comprising the step of delivering and/or implanting a device according to the invention to a position within the heart of a patient in need thereof in order to replace or support the native mitral valve of said patient.

It will be understood that the treatment options provided by the invention are not limited to the mitral valve, but that a device according to the invention may also be used to treat tricuspid valve regurgitation The device according to the invention can be either surgically implanted or delivered by transcatheter methods. In the latter case, i.e. with a transcatheter method, the device according to the invention is loaded onto a suitable deployment catheter, there being compressed by a retractable sheath or tube or similar. The deployment catheter is inserted into the heart of a patient whose tricuspid or mitral valve needs replacement or support.

When treating the mitral valve, the deployment catheter having the device according to the invention loaded thereon in a compressed state, is advanced trans-apically into the left ventricle crossing the mitral valve to the annulus where it is deployed in order to expand the sealing section inside the annlus of the mitral valve at the copatation line, and the valve-bearing section in the ventricle. Also, the compressed device can be introduced via the femoral vein or Jugular vein into the right atrium and trans-septally to the left atrium where it is deployed in order to expand the sealing section in the annulus and the valve-bearing section in the ventricle. Additionally, the compressed device can be introduced via a small surgical thoracotomy into to the pulmonic vein (right, left, inferior or superior pulmonic vein) to the left atrium where it is deployed in order to expand the sealing section in the annulus and the valve-bearing section in the ventricle.

Upon correct placement, the sheath or the otherwise compressing means is retracted to release the device in a stepwise fashion according to the invention, upon which action the stentframe of the device can expand.

The present invention also relates to the use of the prosthetic valve coaptation enhancement device according to the invention for treating tricuspid valve insufficiency, and a method for treating tricuspid valve insufficiency using the prosthetic valve coaptation enhancement device according to the invention; in the use and the method according to the invention, the prosthetic valve coaptation enhancement device comprises a combination of one or more of the anchoring elements as defined above, wherein according to one embodiment the anchoring element is a stent-based aortic valve prosthesis, coupled to the prosthetic mitral valve coaptation enhancement device via lengthy connecting means to the distal outflow end, the anchoring element is to be placed into the pulmonary valve; according to another embodiment, the anchoring element comprises one or more generally U-shaped attachment arms, the attachment arm is comprising a first end and a second end, respectively, wherein the second end comprises attachment means, preferably selected from a hook, a spike or an arrow, and wherein the attachment arms, via its/their respective first end is/are fixed to the stentframe at proximal inflow end, and via its/their respective second end are capable to anchor the main body in the tissue surrounding the right tricuspid annulus; and according to another embodiment, the anchoring element is an expandable structure that is shaped and designed such, that it is positionable within the right atrial appendage.

Further advantages and features of the invention are set forth in the following description and in the attached figures.

It will be understood that the aforementioned features and the features still to be explained below can be used not only in the respectively specified combination but also in other combinations or on their own, without departing from the scope of the present invention.

BRIEF DESCRIPTION OF THE DRAWINGS

The aforementioned features of the invention and the features still to be explained below are shown in the figures, in which:

FIG. 4A-I show schematic drawings of different embodiments of the prosthetic mitral valve coaptation enhancement device according to the invention, with different anchoring elements: FIG. 4A-B: anchoring to the apex; FIG. 4C anchoring in the pulmonary veins; FIG. 4D anchoring in the tissue surrounding the native annulus; anchoring in the atrial FIG. 4E or septal FIG. 4F wall; anchoring via an aortic stent FIG. 4G; anchoring via the atrial appendage FIG. 4H; and FIG. 4I anchoring to the apex without piercing.

DESCRIPTION OF PREFERRED EMBODIMENTS

Figure 1:
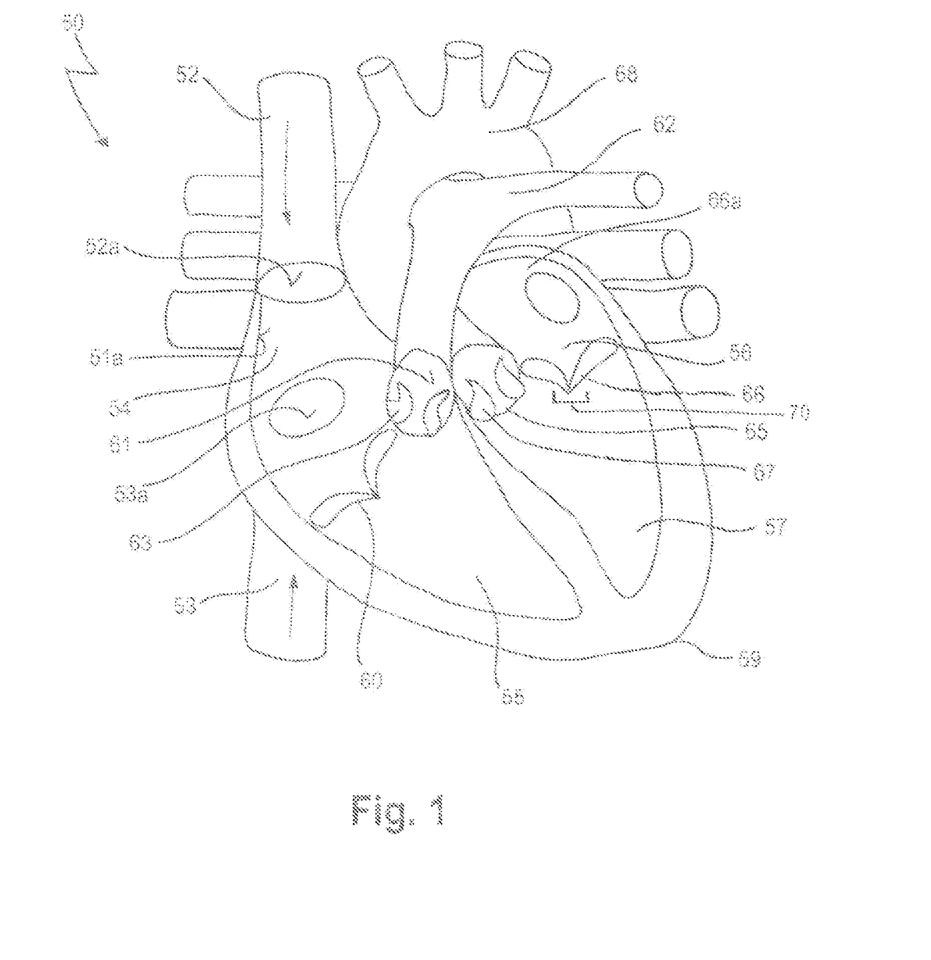
FIG. 1 shows a schematic drawing of a human heart.

In FIG. 1, a human heart 50 is depicted, having a right atrium 54, a right ventricle 55, a left atrium 56 and a left ventricle 57. Also depicted in FIG. 1 is a portion of the vena cava superior 52, entering the heart 50 via the right atrium 54, and a portion of the vena cava inferior 53.

In more detail, the superior vena cava 52 returns the blood from the upper half of the body, and opens into the upper and back part of the right atrium 54, the direction of its orifice 52a being downward and forward. Its orifice 52a has no valve.

The inferior vena cava 53, which has a larger diameter than the superior vena cava 52, returns the blood from the lower half of the body, and opens into the lowest part of the right atrium 54, its orifice 53a being directed upward and backward, and guarded by a rudimentary valve, the valve of the inferior vena cava (Eustachian valve, not shown).

The right ventricle 55 has a triangular in form, and extends from the right atrium 54 to near the apex 59 of the heart 50.

The right atrioventricular orifice (not depicted in FIG. 1) is the large oval aperture of communication between the right atrium 54 and ventricle 55, and is guarded by the tricuspid valve 60 comprising three triangular cusps or segments or leaflets 64.

The opening 61 of the pulmonary artery 62 is circular in form, and is placed above and to the left of the atrioventricular opening; it is guarded by the pulmonary valves 63.

As discussed above, the function of the tricuspid valve 60 is to prevent back flow of blood into the right atrium 54; arrows 70 and 71 indicate normal blood flow into the right atrium 54.

The left atrium 56 is smaller than the right atrium 54. The left ventricle 57 is longer and more conical in shape than the right ventricle 55. The left atrioventricular opening (mitral orifice, not depicted in FIG. 1) is placed to the left of the aortic orifice 65, and is guarded by the bicuspid or mitral valve 66.

The aortic opening 65 is a circular aperture, in front and to the right of the atrioventricular opening, and its orifice is guarded by the three aortic valves 67. Reference number 68 designates the aorta.

Separating the left atrial chamber or left atrium 56 from the left ventricle 57, the mitral valve 66 is, as mentioned above, an atrio-ventricular valve, with the mitral annulus 70 constituting the anatomical junction between the ventricle 57 and the left atrium 56; the annulus 70 also serves as insertion site for the leaflet tissue (not shown).

The normal mitral valve 66 opens when the left ventricle 57 relaxes (diastole) allowing blood from the left atrium 56 to fill the decompressed left ventricle 57. During systole, i.e. when the left ventricle 57 contracts, the increase in pressure within the ventricle 57 causes the mitral valve 66 to close, preventing blood from leaking into the left atrium 56 and assuring that all of the blood leaving the left ventricle is ejected though the aortic valve 67 into the aorta 68 and to the body. Proper function of the mitral valve is dependent on a complex interplay between the annulus 70, leaflets and subvalvular apparatus (not depicted in FIG. 1, respectively).

Figure 2A:
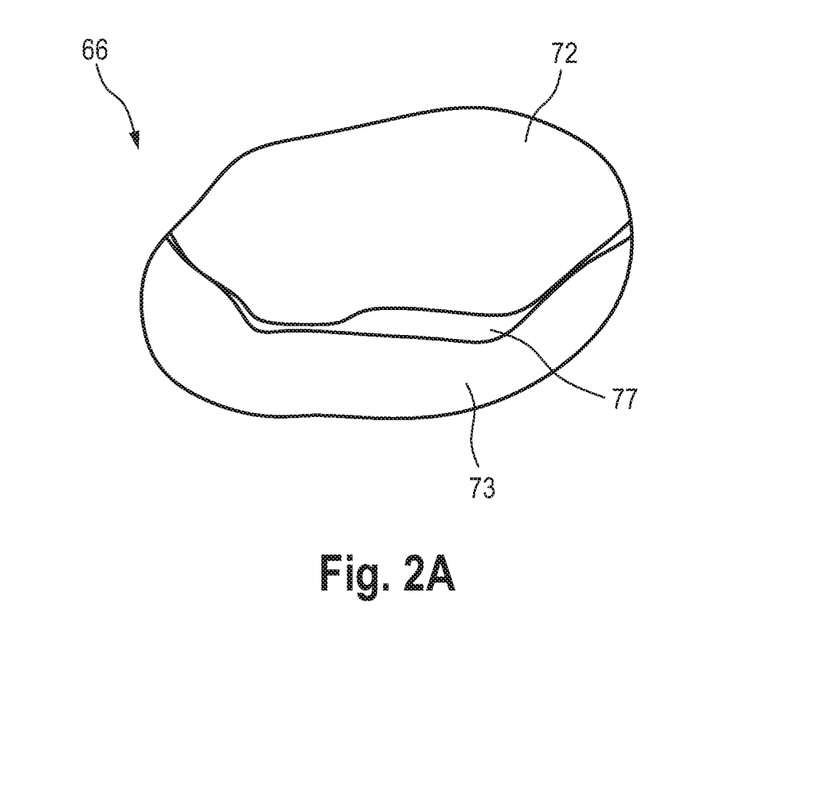
FIG. 2A-B show a schematic drawing of a detailed atrial view of a mitral valve with a malcoaptation of the leaflets without (B) and with (C) a prosthetic mitral valve coaptation enhancement device according to the invention being implanted into the annulus.
Figure 2B:
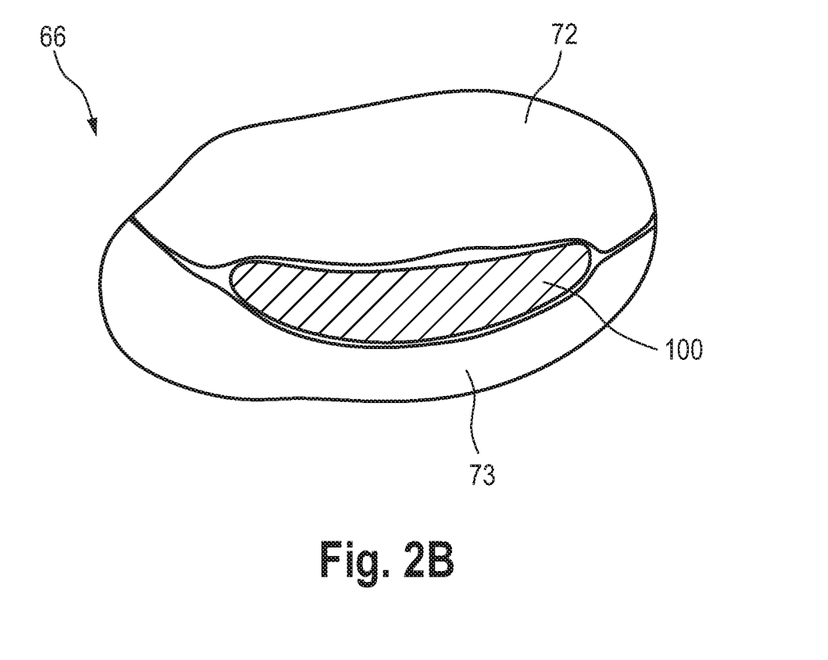

The mitral valve 66 has two leaflets 72, 73 (see FIG. 2), i.e. the anterior 72 and the posterior leaflet 73. As mentioned above, the anterior leaflet 72 has a semicircular shape, and the posterior leaflet 73 has a quadrangular shape. The motion of the anterior leaflet 72 defines an important boundary between the inflow and outflow tracts of the left ventricle 57. The anterior leaflet 72 is attached to two fifths of the annular circumference, while the posterior leaflet 73 is attached to approximately three fifths of the annular circumference. The posterior leaflet 73 has typically two well defined indentations which divide the leaflet 73 into three individual scallops; the indentations aid in posterior leaflet opening during systole.

On the atrial surface of the leaflets 72, 73 there are two zones, the peripheral smooth zone 74 and the central coaptation 75 zone. The two areas 74, 75 are separated by the gently curved coaptation line 76 between the two leaflets 72, 73 evident from atrial view.

Mitral valve 66 regurgitation is present when the valve 66 does not close completely, causing blood to leak back into the left atrium 56.

FIG. 2A shows a schematic drawing of an atrial view onto the mitral valve 66 with malcoapting leaflets 72, 73, the valve not being supported by a prosthetic device according to the invention. As can be seen in FIG. 2A, due to the malcoapting leaflets 72, 73 of the mitral valve 68, a space 77 is left between them, allowing blood flow back into the left atrium upon systole, which is called mitral valve regurgitation.

Figure 3A:
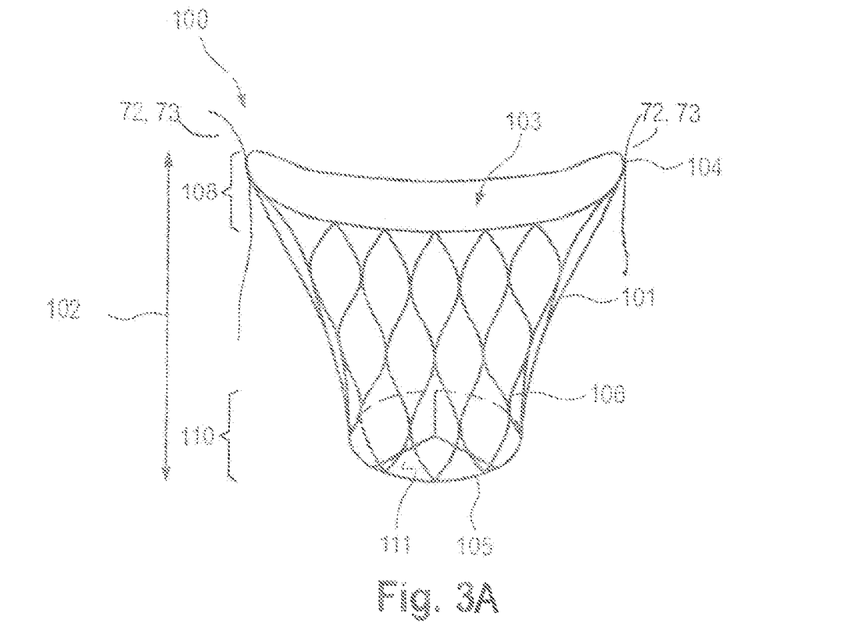
FIG. 3A-B show a schematic drawing of an exemplary non-implanted embodiment of a prosthetic mitral valve coaptation enhancement device according to the invention in the expanded form.
Figure 3B:
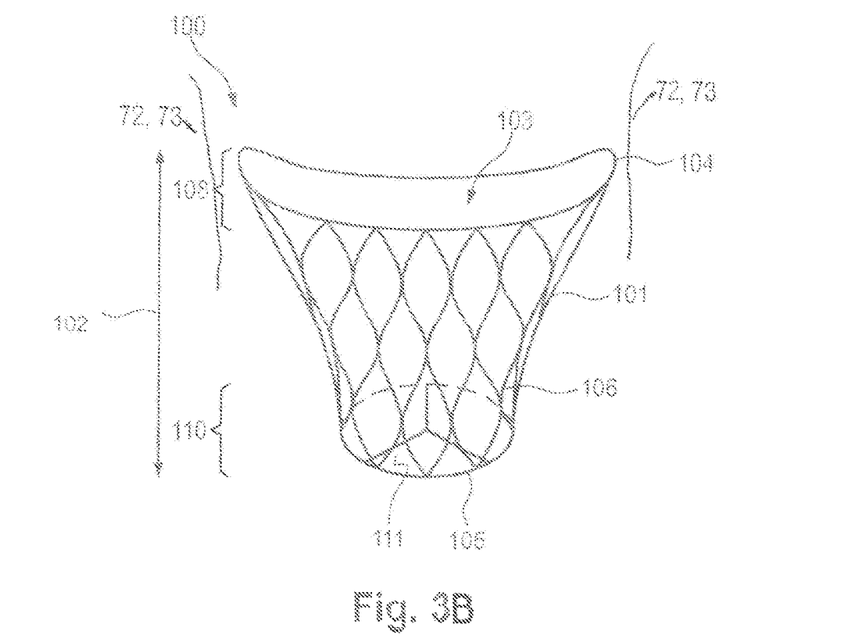

With the device according to the invention, mitral valve regurgitation can be treated, and placement of an exemplary embodiment 100 of the device according to the invention into the diseased mitral valve of FIG. 2A is depicted in the attached FIG. 28, which is also shown in more detail in FIG. 3A-3B.

In the exemplary embodiment of the prosthetic device 100 according to the invention as shown in FIG. 3A-3B, the device 100 is depicted in its expanded state, i.e. the state the device has when implanted into the heart of the patient to be treated. On the other hand, the compressed state is the state the device 100 is in when being loaded onto a transcatheter delivery system compressing the device 100 for introduction via blood vessels of the body.

The device 100 has, a main body 101, comprising a length 102 and a lumen 103, which lumen is defined between a proximal or inflow end 104 and a distal or outflow end 105. The main body 101 consists of a stentframe 106, which has a sealing section 108 and a valve-bearing section 110 carrying a valve element 111.

As can be seen in FIG. 3A-3B, the stentframe 106 has diamond-shaped cells, and has a Substantially cylindrical form. The inflow end 104 has a substantially circular, D or crescent shape, adapting to the coaptation zone 75 of the leaflets 72, 73. The D-shape transitions into a round cross section of the stentframe 106 towards the distal end 105, thus generating the Substantially cylindrical shape of the device. The valve element 111 is located at the distal end 105 of the device. In the embodiment shown in FIG. 3A-3B, the anchoring element 120 is not shown.

Figure 4A:
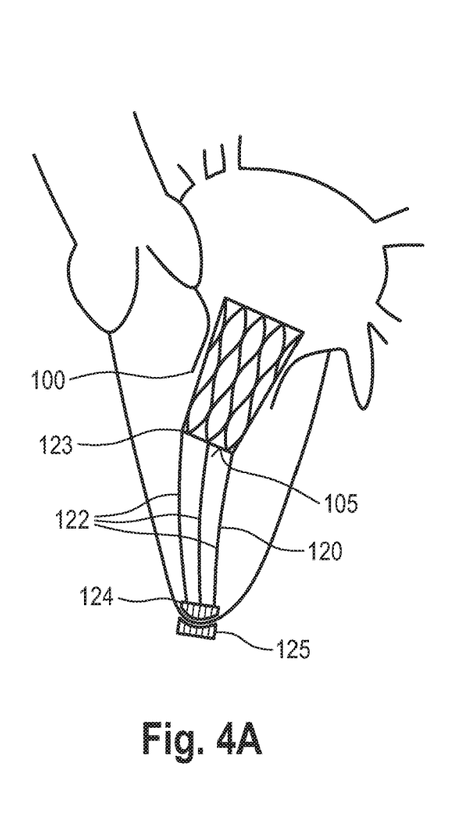

FIG. 4A-I show different embodiments for anchoring elements 120 of the device 100 according to the invention, wherein the placement of the device 100 in the annulus of the mitral valve of a patient's heart (without reference numerals for the sake of clarity) is depicted, respectively, to show the respective anchoring mechanism of the different embodiments:

In FIG. 4A, device 100 according to the invention comprises, as anchoring element 120, three lengthy connecting elements 122 each comprising a first end 123 and a second end 124. With their respective first end 123, the connecting elements 122 are connected to the distal (outflow) end of main body 101; the connecting elements 122 are of a generally rigid material and are, via their second end 124 fixed to a plug element 125, the plug element 125 piercing the apex of the heart.

The plug element 125 can be of any inert suitable material that is commonly used in connection with surgical procedures and intended for implantation in the heart of a patient.

Figure 4B:
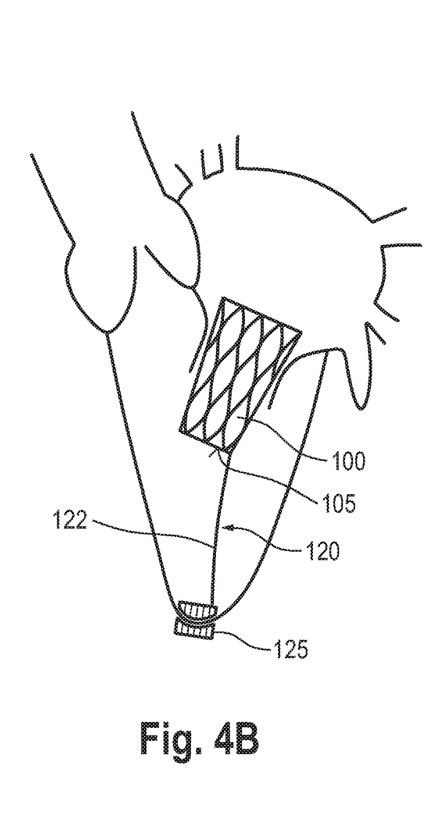

FIG. 4B shows an embodiment, where only one bar 122 is used to anchor the device 100 in the annulus of a mitral valve, whereby also the connecting element 122 shown in FIG. 4B is fixed in the ventricular apex via a plug 125.

Figure 4C:
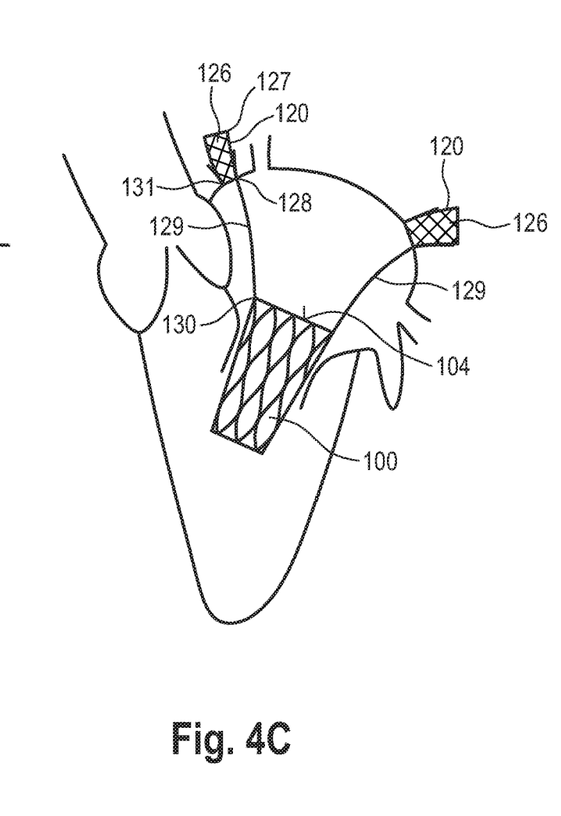

FIG. 4C shows an embodiment, where the device 100 is anchored in the heart via two expandable structures 126, e.g. self-expanding stent-structures, and substantially rigid connecting elements 129. The expandable structures 126 each comprise a first end 127 and a second end 128, and the substantially rigid connecting elements 129 also comprise a first end 130 and a second end 131, respectively. The respective first ends 130 of the ligament means 129 are fixed to the atrial end 104 of the main body 10, and the respective second ends 131 of the substantially rigid connecting elements 129 are fixed to the second ends 128 of the expandable structures 126, thus connecting the expandable structures with the device 100 of the invention, and, as a consequence, anchoring it in the heart.

Figure 4D:
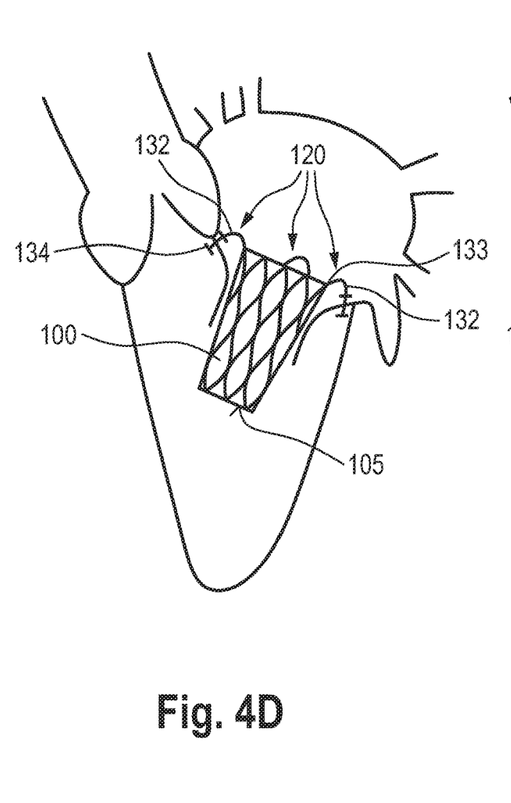

FIG. 4D shows a further embodiment for an anchoring element 120 in connection with the device 100 according to the invention. The anchoring element 120, in FIG. 4D, is represented by generally U-shaped attachment arms 132, each of which has a first and a second end 133, 134, the second ends 134 comprising attachment means, preferably selected from a hook, a spike or an arrow, wherein the attachment arms 132, via their first respective end 133 is fixed to the stentframe 106 at the proximal inflow end 104 of the main body 101, and are, via their respective second ends 134, able to anchor the main body in the tissue surrounding the mitral annulus, e.g. via piercing this tissue.

Figure 4E:
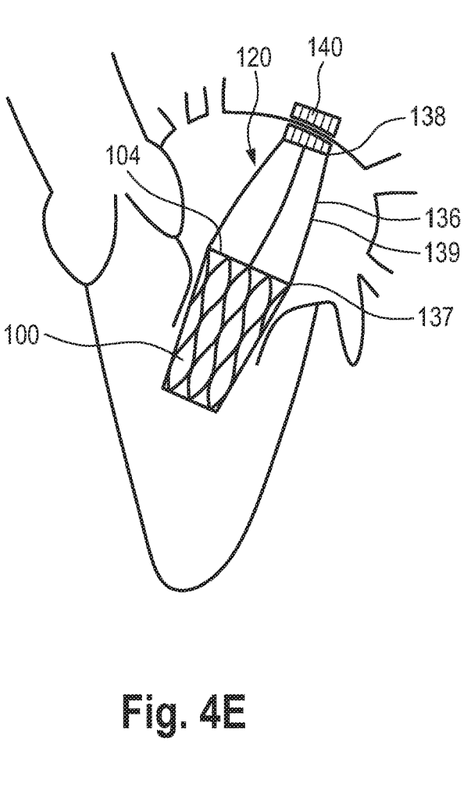

FIG. 4E shows another embodiment for an anchoring element 120 in connection with the device 100 according to the invention. Here, the anchoring element 120 comprises three atrial lengthy connecting elements or means 136, which atrial connecting elements or means 136 comprise a first end 137 and a second end 138, and a length 139 extending there between. The first ends 137 are coupled to the proximal inflow end 104 of the main body 101, and the second ends 138 are coupled to the atrial wall via a plug element 140, which plug element pierces the atrial wall, thereby anchoring the device in the heart.

Figure 4F:
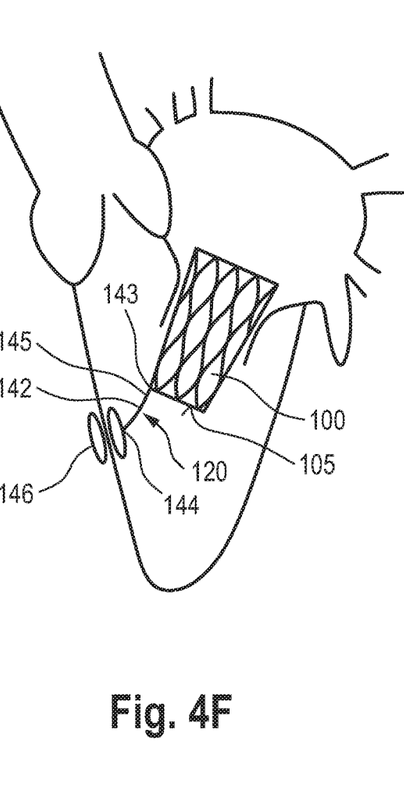

FIG. 4F shows another embodiment for an anchoring element 120 in connection with the device 100 according to the invention. Here, the anchoring element 120 comprises a septal connecting element/means 142 comprising a first end 143 and a second end 144 and a length 145 extending there between. Via its first end 143, the connecting element 142 is coupled to the distal end 105 of the main body 101, and, via its second end 142 and a plug element 148 to the septal wall, thereby piercing the septal wall and anchoring the device 100 according to the invention.

Figure 4G:
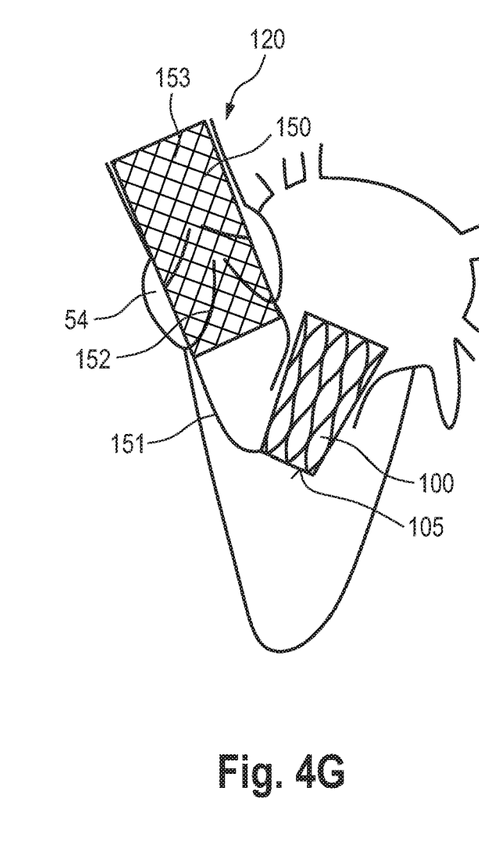

FIG. 4G shows yet another embodiment for an anchoring element 120 in connection with the device 100 according to the invention. Here, the anchoring element 120 is a stent-based aortic valve prosthesis 150, coupled to the prosthetic mitral valve coaptation enhancement device 100 via connecting means 151 to the distal outflow end 105. The aortic valve prosthesis 150, which is to be positioned in the aortic root comprises a stentframe 153 and, as the case may be, i.e. optionally, a biological valve 152. With this embodiment, both native valves. i.e. the native aortic valve 60 and the native mitral valve 66 can be supported/replaced.

Figure 4H:
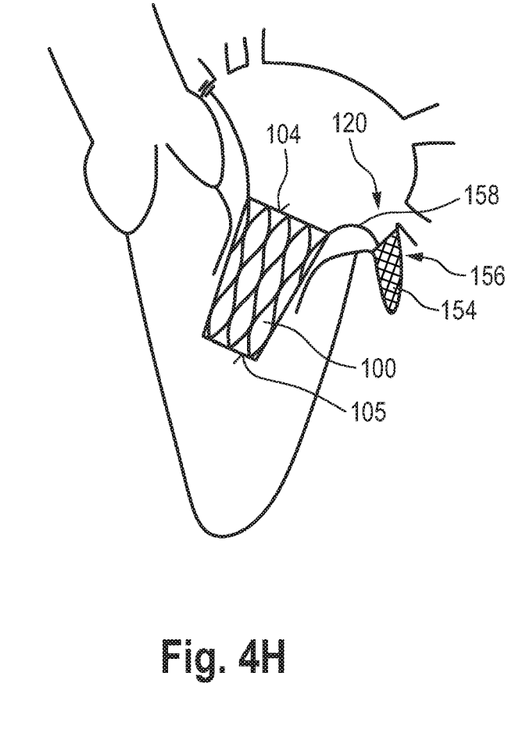

FIG. 4H shows another embodiment for an anchoring element 120 in connection with the device 100 according to the invention. Here, the anchoring element 120 is an expandable structure 154 that is shaped and designed such, that it is positioned within the left atrial appendage 156. The anchoring device 120 shown here also comprises flexible lengthy connecting means 158 coupling the expandable structure 154 with the proximal inflow end 104 of the main body 101.

Figure 4I:
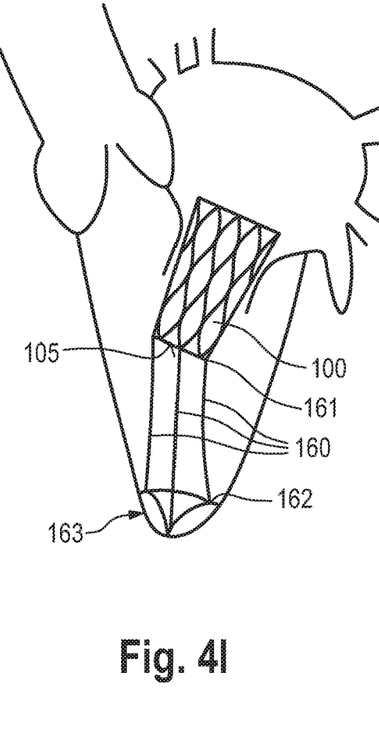

FIG. 4I shows another embodiment for an anchoring element 120 in connection with the device 100 according to the invention. Here, the anchoring element 120 comprises connecting elements 160, having a first end 161, and a second end 162 extending there between, wherein the elements 160, via their respective first ends 161, are connected to the distal end 105 of the main body 101. Their respective second ends 162 are fixed to a clamping element 163, fixing the second ends 162 intraventricularly without piercing the apex.

What is claimed is:

1. A prosthetic mitral valve coaptation enhancement device for implanting at the native mitral valve region of a heart, wherein the native mitral valve, having a native annulus and native valve leaflets, can still perform a closing movement, and wherein the prosthetic mitral valve coaptation enhancement device comprising:
    a main body consisting of a stentframe and a valve element attached thereto, the main body comprising a length and a lumen being defined by a proximal end and a distal end, and configured for placement within the native mitral valve region of the heart, the stentframe being radially compressible to a radially compressed state for delivery into the heart and self-expandable from the compressed state to a radially expanded state, wherein the main body has a sealing section and a valve-bearing section, the valve-bearing section carrying a valve element:
    wherein
    the shape of the sealing section of the main body, when compressed by the native valve leaflets, has a form that is adapted to the coaptation zone of the native mitral valve during systole, that
    in the sealing section of the main body, the radial rigidity of the stentframe is lower than the radial rigidity of the valve-bearing section; and that
    the sealing section of the main body is configured such that it is smaller than the native annulus of the heart into which the prosthetic mitral valve coaptation enhancement device is to be implanted and such that it contacts the native leaflets only during systole, thereby sealing the mitral annulus during systole and permitting filling of the ventricle through and alongside the prosthetic mitral valve coaptation enhancement device during diastole, thereby minimizing the gradient between the left atrium and ventricle;
    and that the prosthetic mitral valve coaptation enhancement device further comprises at least one substantially rigid anchoring element, which anchoring element is coupled to the main body and is capable to anchor the main body within the native mitral valve region of a heart.

2. The prosthetic mitral valve coaptation enhancement device of claim 1, wherein the stentframe in the sealing section, in its expanded state, is substantially circular, D- or crescent-shaped and is adapted to the shape of and designed to be placed at the coaptation line of the native valve, wherein the crescent-shape transitions along the length of the main body towards the ventricular section into a substantially round shape.

3. The prosthetic mitral valve coaptation enhancement device of claim 1, wherein the stentframe in the sealing section consists of a flexible structure such, that, in the compressed state, it conforms to the coaptation zone of the native mitral valve during systole, wherein the stentframe, in the sealing section, has a flexibility and rigidity that is lower than the flexibility and rigidity of the valve-bearing section.

4. The prosthetic mitral valve coaptation enhancement device of claim 1, wherein it has a size enabling the sealing section being positionable at the level of the native mitral valve leaflets and the valve-bearing section being positionable distally in the left ventricle.

5. The prosthetic mitral valve coaptation enhancement device of claim 1, comprising a combination of one or more of the anchoring elements as defined in claim 4.

6. The prosthetic mitral valve coaptation enhancement device of claim 1, wherein the anchoring element comprises one or more lengthy substantially rigid connecting elements, the connecting elements comprising a first end, a second end and a length extending there between, wherein the connecting elements, via its/their respective first end/s is/are coupled to the valve-bearing section via the distal outflow end of the main body, and, via its/their respective second end/s, is/are coupleable to the ventricular apex.

7. The prosthetic mitral valve coaptation enhancement device of claim 6, wherein the second end of the anchoring element is coupled to a plug element, which is sized and configured to be positionable in the ventricular apex of the heart, thereby piercing the apex.

8. The prosthetic mitral valve coaptation enhancement device of claim 6, wherein the anchoring element comprises one lengthy substantially rigid connecting element.

9. The prosthetic mitral valve coaptation enhancement device of claim 6, wherein the anchoring element comprises three lengthy substantially rigid connecting elements.

* * * * *